United States Patent
Li et al.

[11] Patent Number: 6,066,126
[45] Date of Patent: May 23, 2000

[54] PRECURVED, DUAL CURVE CARDIAC INTRODUCER SHEATH

[75] Inventors: Hong Li, Cupertino; John W. Gaiser, Mountain View, both of Calif.

[73] Assignee: Medtronic, Inc., Minneapolis, Minn.

[21] Appl. No.: 08/993,217

[22] Filed: Dec. 18, 1997

[51] Int. Cl.[7] .................................................. A61M 25/00
[52] U.S. Cl. ......................... 604/532; 604/523; 604/528
[58] Field of Search ..................... 604/523, 264, 604/530, 528, 532; 138/118

[56] References Cited

U.S. PATENT DOCUMENTS

| | | |
|---|---|---|
| 4,033,331 | 7/1977 | Guss et al. . |
| 4,117,836 | 10/1978 | Erikson . |
| 4,169,464 | 10/1979 | Obrez . |
| 4,405,314 | 9/1983 | Cope . |
| 4,547,193 | 10/1985 | Rydell . |
| 4,548,206 | 10/1985 | Osborne . |
| 4,569,347 | 2/1986 | Frisbie . |
| 4,581,017 | 4/1986 | Sahota . |
| 4,581,025 | 4/1986 | Timmermans . |
| 4,637,396 | 1/1987 | Cook . |
| 4,694,838 | 9/1987 | Wijayarthna et al. . |
| 4,747,840 | 5/1988 | Ladika et al. . |
| 4,920,980 | 5/1990 | Jackowski . |
| 5,016,640 | 5/1991 | Ruiz . |
| 5,058,595 | 10/1991 | Kern . |
| 5,120,323 | 6/1992 | Shockey et al. . |
| 5,122,115 | 6/1992 | Marks . |
| 5,147,315 | 9/1992 | Weber . |
| 5,163,921 | 11/1992 | Feiring . |
| 5,188,619 | 2/1993 | Myers ...................................... 604/280 |
| 5,195,990 | 3/1993 | Weldon . |
| 5,203,776 | 4/1993 | Durfee . |
| 5,215,540 | 6/1993 | Anderhub . |
| 5,231,994 | 8/1993 | Harmjanz . |
| 5,243,996 | 9/1993 | Hall . |
| 5,290,229 | 3/1994 | Paskar . |
| 5,299,574 | 4/1994 | Bower . |
| 5,299,575 | 4/1994 | Sandridge . |
| 5,304,131 | 4/1994 | Paskar . |
| 5,306,263 | 4/1994 | Voda . |
| 5,322,509 | 6/1994 | Rickerd . |
| 5,328,480 | 7/1994 | Melker et al. . |

(List continued on next page.)

FOREIGN PATENT DOCUMENTS

| | | |
|---|---|---|
| 930636 | 7/1973 | Canada . |
| 0 256 478 A1 | 2/1988 | European Pat. Off. . |
| 0 453 008 A1 | 10/1991 | European Pat. Off. . |
| 0 454 264 A1 | 10/1991 | European Pat. Off. . |
| 0 670 168 A1 | 9/1995 | European Pat. Off. . |
| 0 711 573 A1 | 5/1996 | European Pat. Off. . |
| 0 727 239 A2 | 8/1996 | European Pat. Off. . |
| 0 727 263 A1 | 8/1996 | European Pat. Off. . |
| 0277366 | 12/1997 | European Pat. Off. . |

*Primary Examiner*—Corrine McDermott
*Assistant Examiner*—Cris L. Rodriguez
*Attorney, Agent, or Firm*—Daniel W. Latham; Harold R. Patton

[57] ABSTRACT

A precurved cardiac introducer sheath (4) includes an elongate, hollow body having main and tip portions (24, 22). The tip portion includes first through fifth segments (26, 28, 30, 32, 34). The first, second, and third segments lie in a first plane (36) while the fourth and fifth segments lie in a second plane (38) oriented at a second angle (37) of about ±10 to 170° to the first plane. The second segment defines an arc extending along a first, included angle of about 90–110° while the fourth segment defines an arc extending along a third, included angle of about 90–140°. The first, third, and fifth segments are preferably generally straight segments. The precurved introducer sheath is preferably configured to direct the electrophysiology catheter (18) directly at the posterior region (52) of the left atrium (40). The precurved introducer sheath is preferably housed within an outer introducer sheath (46) having a radially deflectable distal end (46), or a fixed distal curve.

8 Claims, 2 Drawing Sheets

U.S. PATENT DOCUMENTS

| | | | |
|---|---|---|---|
| 5,348,545 | 9/1994 | Shani et al. | |
| 5,380,304 | 1/1995 | Parker. | |
| 5,403,292 | 4/1995 | Ju. | |
| 5,427,119 | 6/1995 | Swartz et al. | |
| 5,445,625 | 8/1995 | Voda | 604/281 |
| 5,471,986 | 12/1995 | Ishimura et al. | |
| 5,476,453 | 12/1995 | Mehta. | |
| 5,487,729 | 1/1996 | Avellanet et al. | |
| 5,492,530 | 2/1996 | Fischell et al. | |
| 5,497,774 | 3/1996 | Swartz et al. | |
| 5,531,721 | 7/1996 | Pepin et al. | |
| 5,542,938 | 8/1996 | Avellanet et al. | |
| 5,545,151 | 8/1996 | O'Connor et al. | 604/282 |
| 5,564,440 | 10/1996 | Swartz et al. | |
| 5,569,218 | 10/1996 | Berg. | |
| 5,584,821 | 12/1996 | Hobbs et al. | 604/280 |
| 5,599,325 | 2/1997 | Ju et al. | |
| 5,603,704 | 2/1997 | Brin et al. | 604/281 |
| 5,658,263 | 8/1997 | Dang et al. | 604/280 |
| 5,814,028 | 9/1998 | Swartz et al. | 604/280 |
| 5,833,673 | 11/1998 | Ockuly et al. | 604/281 |
| 5,836,925 | 11/1998 | Soltesz | 604/280 |
| 5,836,926 | 11/1998 | Peterson et al. | 604/282 |
| 5,846,229 | 12/1998 | Berg | 604/281 |
| 5,876,385 | 3/1999 | Ikari et al. | 604/280 |
| 5,879,296 | 3/1999 | Ockuly et al. | 600/374 |
| 5,885,247 | 3/1999 | Slagboom | 604/95 |
| 5,885,259 | 3/1999 | Berg | 604/281 |
| 5,891,057 | 4/1999 | Chaisson et al. | 600/585 |
| 5,891,109 | 4/1999 | Inoue et al. | 604/265 |
| 5,897,537 | 4/1999 | Berg et al. | 604/282 |
| 5,902,287 | 5/1999 | Martin | 604/280 |
| 5,902,289 | 5/1999 | Swartz et al. | 604/281 |
| 5,916,209 | 6/1999 | Mick | 604/523 |
| 5,941,872 | 10/1999 | Berg | 604/523 |
| 5,957,911 | 9/1999 | Nesto | 604/532 |
| 5,971,974 | 10/1999 | Keisz | 604/523 |

PRECURVED, DUAL CURVE CARDIAC INTRODUCER SHEATH

BACKGROUND OF THE INVENTION

This invention relates to introducer sheaths used to introduce an electrophysiology catheter into the left atrium of the heart through a transseptal puncture and then direct the catheter to the target region within the left atrium. The invention is especially useful for directing the electrophysiology catheter to the posterior region of the left atrium.

The heart includes a number of pathways which are responsible for the propagation of signals necessary for normal electrical and mechanical function. The present invention is concerned with treatment of tachycardia, abnormally rapid rhythms of the heart caused by the presence of an arrhythmogenic site or accessory pathway which bypasses or short circuits the normal pathways in the heart. Tachycardias may be defined as ventricular tachycardias (VTs) and supraventricular tachycardias (SVTs). VTs originate in the left or right ventricle and are typically caused by arrhythmogenic sites associated with or without underlying heart disease. SVTs originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, drugs typically only mask the symptoms and do not cure the underlying cause. Implantable devices, on the other hand, usually can correct an arrhythmia only after it occurs. Surgical and catheter-based treatments, in contrast, will actually cure the problem usually by ablating the abnormal arrhythmogenic tissue or accessory pathway responsible for the tachycardia. The catheter-based treatments rely on the application of various destructive energy sources to the target tissue including direct current electrical energy, radiofrequency electrical energy, laser energy, and the like.

Of particular interest to the present invention, are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue to ablate a region of the tissue which forms part of the arrhythmogenic site or the accessory pathway. By successfully destroying that tissue, the abnormal signaling patterns responsible for the tachycardia cannot be sustained. Methods and systems for performing RF ablation by controlling temperature at the ablation site are described in U.S. Pat. No. 5,540,681 entitled "Method and System for Radiofrequency Ablation of Tissue."

Catheters designed for mapping and ablation frequently include a number of individual electrode bands mounted to the distal tip of the catheter so as to facilitate mapping of a wider area in less time, or to improve access to target sites for ablation. Such catheters are described in U.S. Pat. No. 5,445,148 entitled "Intracardiac Electrical Potential Reference Catheter." Mapping and ablation catheters may facilitate rotational positioning of the distal tip, either by rotating the entire catheter from the proximal end, or by exerting torque on a core wire secured to the distal tip without rotating the catheter body itself. See U.S. Pat. No. 5,545,200 entitled "Steerable Electrophysiology Catheter." Introducer catheters or sheaths having precurved distal ends have been used for guiding cardiac catheters as well as other types of catheters. See, for example, U.S. Pat. No. 5,147,315 and European Patent Application Publication No. 0670168.

SUMMARY OF THE INVENTION

The present invention is directed to a cardiac introducer sheath especially adapted for accessing the posterior region of the left atrium of the heart.

The cardiac introducer sheath includes an elongate, hollow body having a main portion and a precurved tip portion. The tip portion includes first through fourth, and preferably first through fifth, segments. The first, second, and third segments lie in a first plane while the fourth and fifth segments lie in a second plane oriented at a second, plane angle to the first plane. The second segment defines an arc extending along a first, arc angle while the fourth segment defines an arc extending along a third, arc angle. The first and third segments are preferably generally straight segments.

The precurved introducer sheath is preferably constructed so that the electrophysiology catheter is directed at various portions of the left atrium, and in particular to the posterior region of the left atrium. This is preferably achieved by making a first and third segments generally straight and the second segment with a first, arc angle of about 70–90° and a fourth segment with a third, arc angle of about 40–90°. Having such relatively sharp curves for the second and fourth segments also permit the introducer sheath to be made of softer materials because the tip portion is more resistant to straightening at body temperatures caused by the passage of the electrophysiology catheter through the introducer sheath. The relatively sharp curves for the second and fourth segments and the use of a relatively short fifth segment leaves room for a relatively long electrode-carrying tip of a linear ablation catheter to maneuver.

Other features and advantages of the invention will appear from the following description in which the preferred embodiments have been set forth in detail in conjunction with the accompanying drawings.

DESCRIPTION OF THE PREFERRED EMBODIMENT

Figure 1:
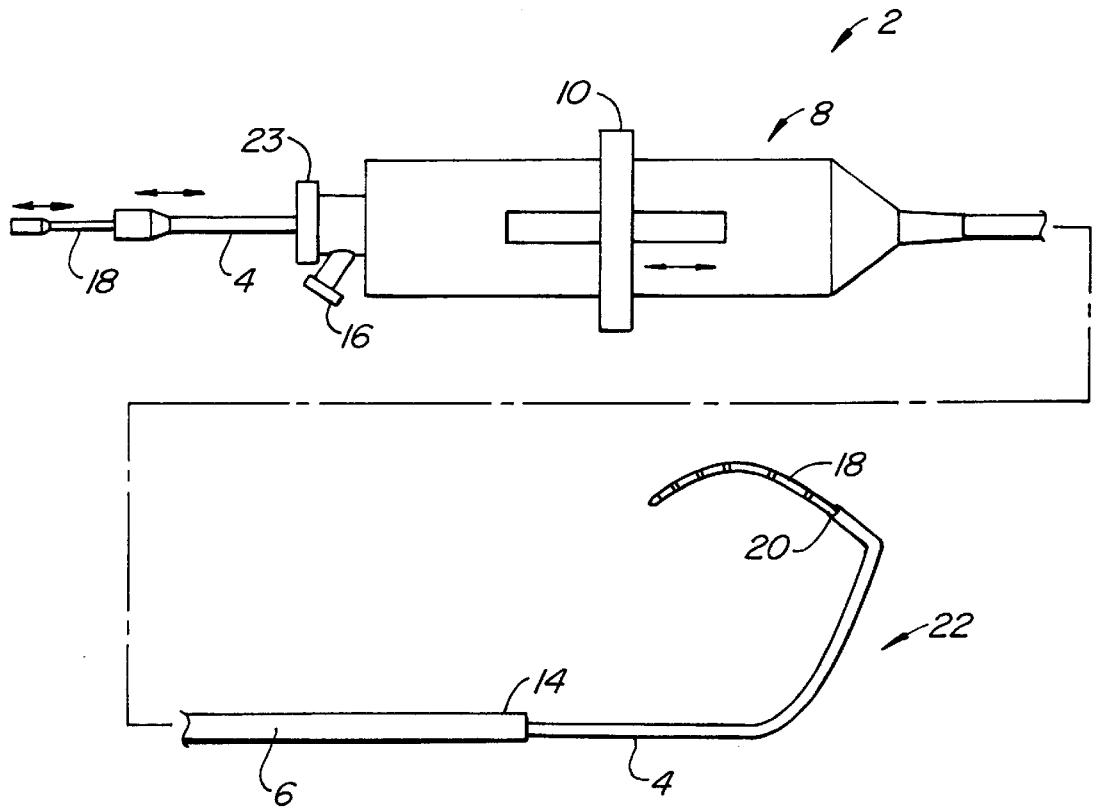
FIG. 1 illustrates a catheter assembly including a precurved cardiac introducer sheath made according to the invention.

FIG. 1 illustrates a catheter assembly 2 including a precurved, inner cardiac introducer sheath 4 made according to the invention. Cardiac introducer sheath 4 is housed within an outer cardiac introducer sheath 6 extending from a proximal end adaptor or handle 8. Handle 8 is used if the outer sheath 6 has an active deflectable tip 14. Handle 8 include a manipulator 10, used to radially deflect tip 14, and a fluid port 16 to permit flushing of the lumen of sheath 6 with saline as is generally conventional. A deflectable electrophysiology catheter 18 passes through inner cardiac introducer sheath 4 and out through a distal open end 20 of the tip portion 22 of introducer sheath 4. Inner sheath 4, with catheter 18 therein, is introduced into outer sheath 6 through the open proximal end 23 of handle 8. Sheath 4 also typically includes a fluid port to permit flushing of its lumen.

Figure 2:
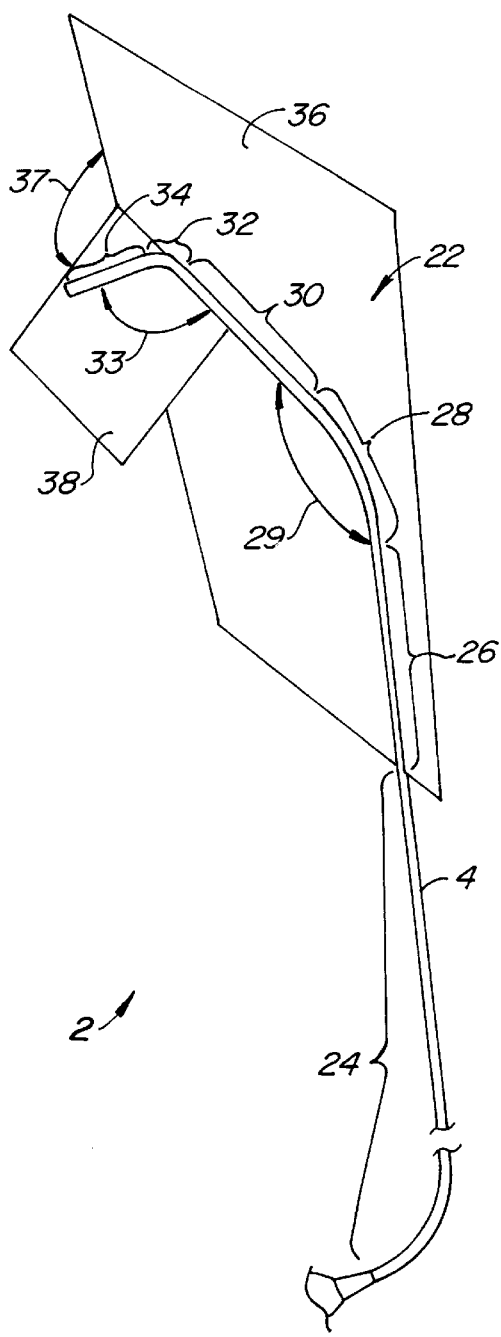
FIG. 2 is a simplified view of the introducer sheath of FIG. 1 in a first configuration.

Turning now also to FIG. 2, tip portion 22 is seen to extend from the main portion 24 of introducer sheath 4. Tip portion 22 includes first, second, third, fourth, and fifth segments 26, 28, 30, 32, and 34. First, third, and fifth segments 26, 30, and 34 are all preferably straight while second and fourth segments 28 and 32 are arcuate segments. Segments 26, 30, and 34 preferably have lengths of about 70 cm to 90 cm, 4 cm to 6 cm, and 0.5 cm to 2.0 cm, respectively. More preferably, segments 26, 30, and 34 have lengths of about 75 cm to 80 cm, 4.5 cm to 5.5 cm, and 0.7 cm to 1.3 cm, respectively. First, second, and third segments 26, 28, and 30 lie in a first plane 36 while fourth and fifth segments 32, 34 lie in a second plane 38. Second segment 28 defines a first, arc angle of about 70–90°, which corresponds to a first, included angle 29 of about 90–110°. First and second planes 36, 38 are oriented at a second, plane angle 37 of about ±10° to ±170° to one another. Fourth segment 32 defines a third, arc angle of about 40–90°, which corresponds to a third, included angle 33 of 90–140°. The second and fourth segments 28,32 define areas of constant radii.

Figure 4:
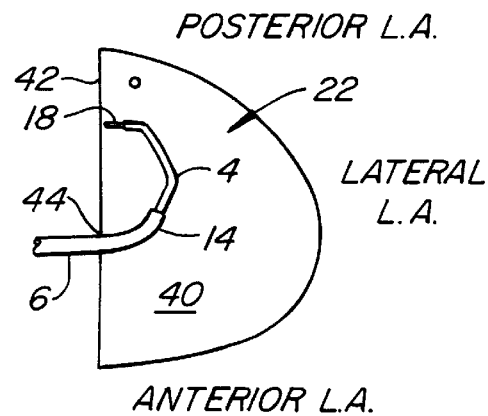
FIG. 4 schematically illustrates the distal portions of the outer and inner cardiac introducer sheaths of FIG. 1 passing through the atrioventricular septum with the distal end of the outer sheath radially deflected and oriented to help direct the tip of the electrophysiology catheter at the posterior region of the left atrium.

Tip portion 22 is configured so to direct electrophysiology catheter 18 towards the various regions of the left atrium. This is illustrated schematically in FIG. 4. Left atrium 40 is shown with outer cardiac introducer sheath 6 passing through the septum 42 at the fossa ovalis 44. Inner sheath 4 can be used alone, that is without outer sheath 6, if desired. As can be seen by comparing FIGS. 1 and 4, the distal end 14 of outer introducer sheath 6 is preferably radially deflectable which not only helps guide outer introducer sheath 6 through the patient's vasculature, with catheter 18 and inner cardiac introducer sheath 4 housed therein, but also helps to provide appropriate positioning for catheter 18. The choice of first, included angle 29 depends upon the size of the heart, and stiffness of the EP catheter to be passed through the sheath. Third, included angle 33 is chosen to have larger included angles (smaller arc angles) over the specified range when it is desired to direct catheter 18 towards pulmonary veins at the lateral side of the left atrium. Smaller included angles (larger arc angles) for the third, included angle 33 are chosen when electrophysiology catheter 18 is to be directed towards the pulmonary veins at the septal side.

Figure 3A:
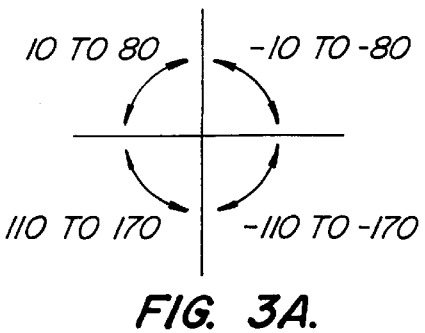
FIG. 3A illustrates the range of angles for the second angle of FIGS. 2 and 3 when looking toward the left atrium.
Figure 3:
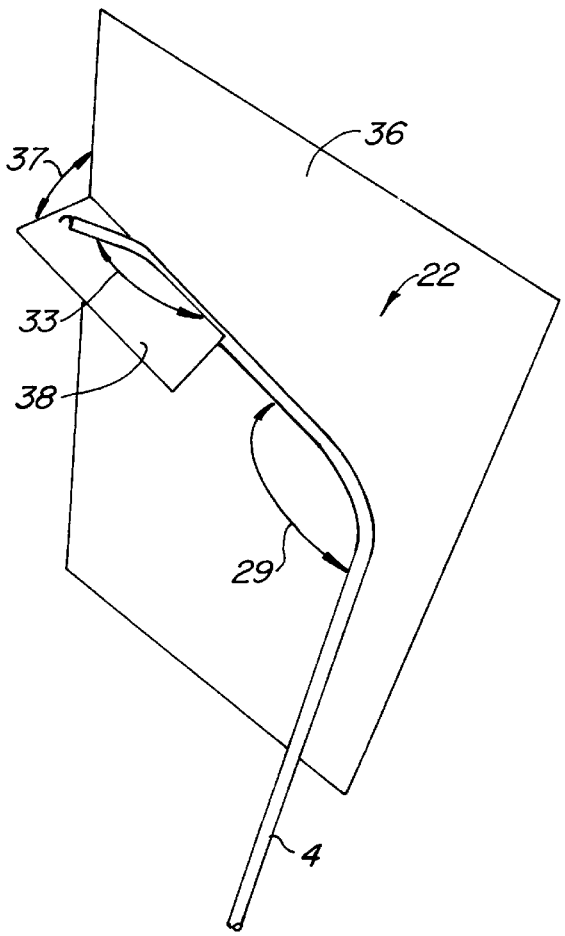
FIG. 3 is similar to FIG. 2 but illustrates the distal portion of the introducer sheath in a second configuration.

Second angle 37 is chosen to be about: (a) plus 10–80° for target regions at the upper left atrium, posterior region; (b) minus 10–80° for the upper left atrium, anterior region; (c) plus 100–170° for the lower left atrium posterior region; and (d) minus 100–170° for the lower left atrium, anterior region. Typical targets for curves (a), (c) include the pulmonary veins. Typical targets for curves (b), (d) include the mitral annulus region. In both FIGS. 2 and 3, second angle 37 is shown to be a positive angle; negative second angles 37 would find fourth and fifth segments 32, 34 extending on the opposite side of first plane 36. FIG. 3A illustrates second angle 37 as it appears when facing the left atrium.

In use, outer cardiac introducer sheath 6 houses precurved inner cardiac introducer sheath 4 which houses electrophysiology catheter 18. A guidewire (not shown) may be used to help guide distal end of outer sheath 6 into left atrium 40 through a puncture in the septum 42 at fossa ovalis 44. Once within left atrium 40, tip portion 22 of inner cardiac introducer sheath 4 is extended from distal end 14. The rotary orientation of sheaths 4, 6 and the shapes and sizes of segments 26, 28, 30, 32, 34 cause distal outer open end 20 of tip portion 22 to be directed at the posterior region 52 of left atrium 40 as suggested in FIG. 4. Radial deflection of distal end 14 of outer sheath 6 to the curved shape of FIG. 4 also helps to direct catheter 18. Deflectable electrophysiology catheter 18 can then be extended through open end 20 to permit the desired electrophysiology procedure, typically mapping followed by ablation, to be carried out in a conventional manner. If catheter 18 is a deflectable catheter, one or more additional manipulators, not shown, could be used to cause the distal end of electrophysiology catheter 18 to be deflected radially into a curve, or both radially into a curve and laterally. Similarly, it may be desired to be able to provide lateral deflection (torsion) for tip portion 22 of precurved inner cardiac introducer sheath 4 and/or for distal end 14 of outer cardiac introducer sheath 6. U.S. Pat. Nos. 5,545,200; 5,397,304; 5,487,757 disclose various structures for radial and lateral deflection of catheter elements.

Any and all patents, applications, and printed publications referred to above are incorporated by reference.

Modification and variation can be made through the disclosed embodiments without departing from the subject of the invention as defined in the following claims. For example, a radially deflectable tip could be replaced by a precurved tip; alternatively, tip 14 of outer sheath 6 could be straight and take the shape of inner sheath 4.

What is claimed is:

1. A left atrium cardiac introducer sheath comprising:

an elongate, hollow body comprising a main portion and a tip portion the tip portion comprising, in order, first, second, third and fourth segments, the first segment extending from the main portion;

the first, second, and third segments lying in a first plane;

the first segment having a length of about 70 cm to 90 cm;

the second segment defining an arc extending along a first, arc angle of about 70° to 90°;

the third segment having a length of about 4 cm to 6 cm;

the fourth segment lying in a second plane, the second plane oriented at a second angle of about ±10° to ±170° to the first plane; and the fourth segment defining an arc extending along a third, arc angle of about 40° to 90°, such that the fourth segment is adapted to enter the left atrium of the heart.

2. The cardiac introducer sheath according to claim 1 wherein the tip portion further comprises a fifth segment extending from the fourth segment.

3. The cardiac introducer sheath according to claim 2 wherein the fifth segment lies in the second plane.

4. The cardiac introducer sheath according to claim 2 wherein the fifth segment has a length of about 0.5 cm to 2 cm.

5. The cardiac introducer sheath according to claim 1 wherein the first and third segments are straight segments.

6. The cardiac introducer sheath according to claim 1 wherein the second and fourth segments defines areas with constant radii.

7. A cardiac introducer sheath assembly comprising:

an inner cardiac introducer sheath comprising:

- an elongate, hollow body comprising a main portion and a tip portion;
- the tip portion comprising, in order, first, second, third and fourth segments, the first segment extending from the main portion;
- the first, second, and third segments lying in a first plane;
- the first segment having a length of about 70 cm to 90 cm:
- the second segment defining an arc extending along a first, arc angle of about 70° to 90°;
- the third segment having a length of about 4 cm to 6 cm:
- the fourth segment lying in a second plane, the second plane oriented at a second angle of about ±10° to ±170° to the first plane; and
- the fourth segment defining an arc extending along a third, arc angle of about 40° to 90°; and
- an outer cardiac introducer sheath comprising an elongate, hollow outer body, containing said inner cardiac introducer, including an outer tip portion and an outer main portion, the outer tip portion being a remotely radially deflectable outer tip portion.

8. The assembly according to claim 7 wherein the outer tip portion takes on a curved shape imparted by said inner cardiac introducer sheath.

* * * * *